US010252269B2

(12) United States Patent
Kung et al.

(10) Patent No.: US 10,252,269 B2
(45) Date of Patent: Apr. 9, 2019

(54) METHODS OF SORTING ACTIVATED T CELLS USING THREE DIMENSIONAL DIELECTROPHORESIS

(71) Applicants: NanoCav, LLC, Culver City, CA (US); NantBio, Inc., Culver City, CA (US)

(72) Inventors: Yu-Chun Kung, Los Angeles, CA (US); Ting-Hsiang Wu, Culver City, CA (US); Peter Sieling, Woodland Hills, CA (US); Kayvan Niazi, Agoura Hills, CA (US)

(73) Assignees: NANTBIO, INC., Culver City, CA (US); NANOCAV, LLC, Culver City, CA (US)

( * ) Notice: Subject to any disclaimer, the term of this patent is extended or adjusted under 35 U.S.C. 154(b) by 0 days.

(21) Appl. No.: 15/816,911

(22) Filed: Nov. 17, 2017

(65) Prior Publication Data
US 2018/0141048 A1    May 24, 2018

Related U.S. Application Data

(60) Provisional application No. 62/424,348, filed on Nov. 18, 2016.

(51) Int. Cl.
*B01L 3/00* (2006.01)
*B03C 5/00* (2006.01)
(Continued)

(52) U.S. Cl.
CPC ..... *B01L 3/502761* (2013.01); *B01L 3/50273* (2013.01); *B03C 5/005* (2013.01);
(Continued)

(58) Field of Classification Search
CPC .......... B01L 3/502761; B01L 3/50273; B03C 5/026; B03C 5/005; C12N 5/0638; C12N 5/0637
See application file for complete search history.

(56) References Cited

U.S. PATENT DOCUMENTS 7,964,078 B2 * 6/2011 Lee ................... B01L 3/502761
204/547
2011/0020459 A1 * 1/2011 Achrol ............. B01L 3/502753
424/520
(Continued)

FOREIGN PATENT DOCUMENTS

WO    2018/094249    * 11/2017

OTHER PUBLICATIONS

Kirschbaum et al., T cell activation on a single-cell level in dielectrophoresis-based microfluidic devices, Journal of Chromatography A, vol. 1202, pp. 83-89. (Year: 2008).*

*Primary Examiner* — Melanie Brown
(74) *Attorney, Agent, or Firm* — Edell, Shapiro & Finnan, LLC

(57) ABSTRACT

Methods and devices are provided for focusing and/or sorting activated T cells. The device comprises a microfluidic channel comprising a plurality of electrodes arranged to provide dielectrophoretic (DEP) forces that are perpendicular to forces from hydrodynamic flows along the channel. The device may be configured to apply voltages to a plurality of electrodes in a first upper region of the microfluidic channel to focus the cells into a single flow, and to apply different voltages to a plurality of electrodes in a second downstream region of the microfluidic channel to sort cells based on size. The output of the microfluidic channel may diverge into multiple channels, wherein cells of various sorted sizes are directed into the appropriate output channel.

25 Claims, 7 Drawing Sheets

(51) Int. Cl.
*C12N 5/0783* (2010.01)
*B03C 5/02* (2006.01)
(52) U.S. Cl.
CPC ............ *B03C 5/026* (2013.01); *C12N 5/0637* (2013.01); *C12N 5/0638* (2013.01); *B01L 2200/0636* (2013.01); *B01L 2200/0652* (2013.01); *B01L 2300/0645* (2013.01); *B01L 2300/0864* (2013.01); *B01L 2300/12* (2013.01); *B01L 2400/0424* (2013.01); *B03C 2201/26* (2013.01)

(56) References Cited

U.S. PATENT DOCUMENTS

| | | | |
|---|---|---|---|
| 2014/0227777 A1* | 8/2014 | Choi | B01L 3/502761 435/309.1 |
| 2016/0331297 A1* | 11/2016 | Voldman | A61B 5/14546 |
| 2017/0291172 A1* | 10/2017 | Kung | B01L 3/502761 |

* cited by examiner

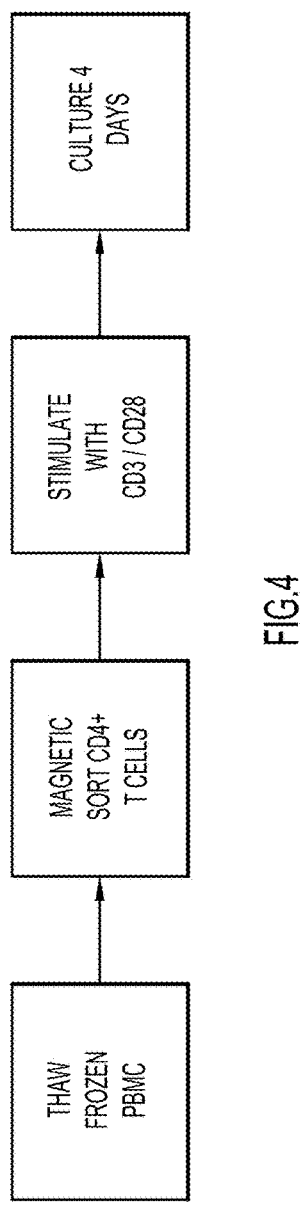
FIG.4
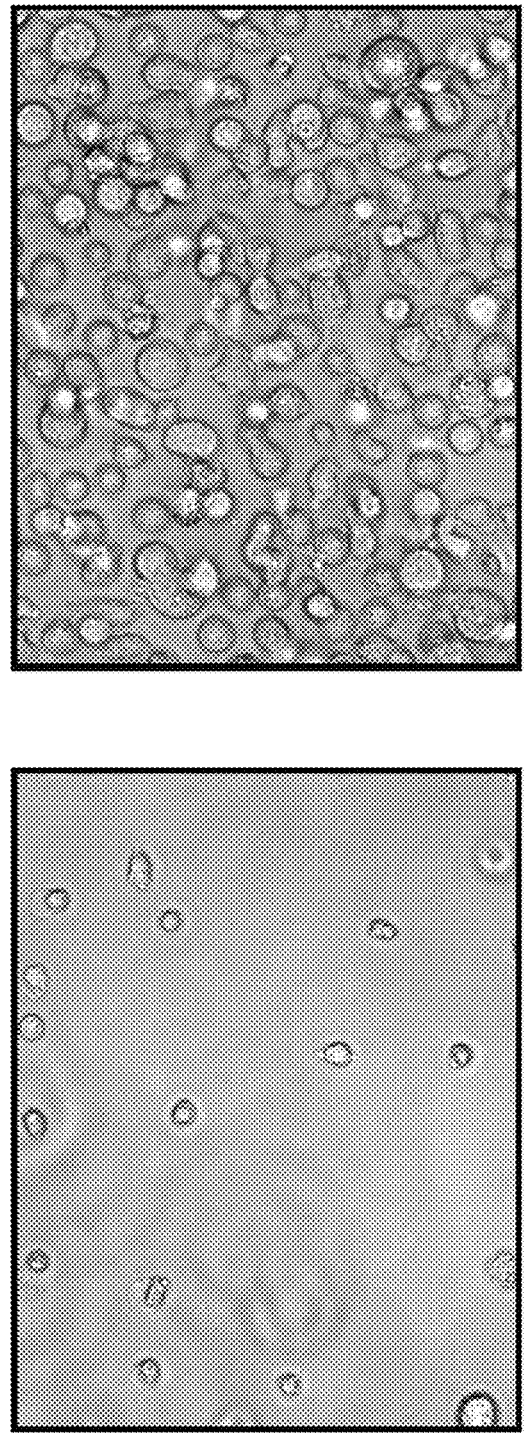
FIG.5A
FIG.5B

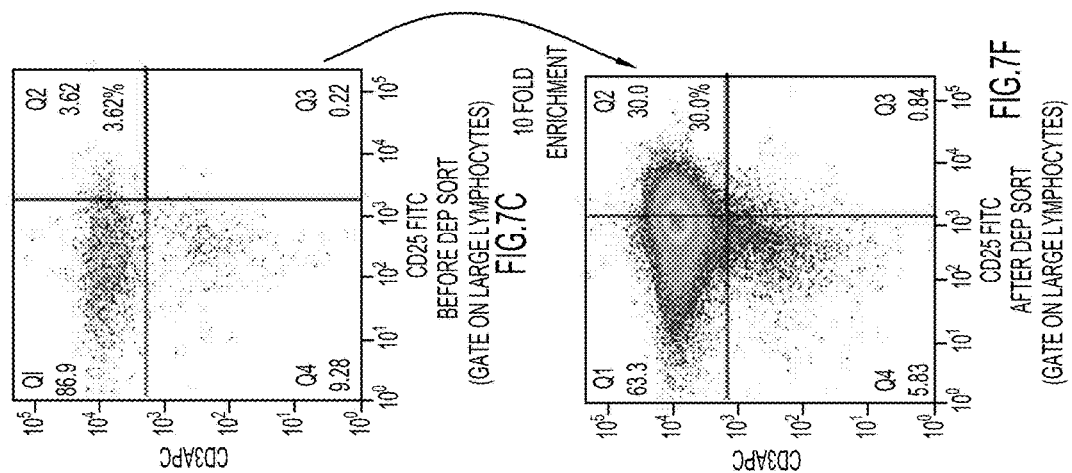
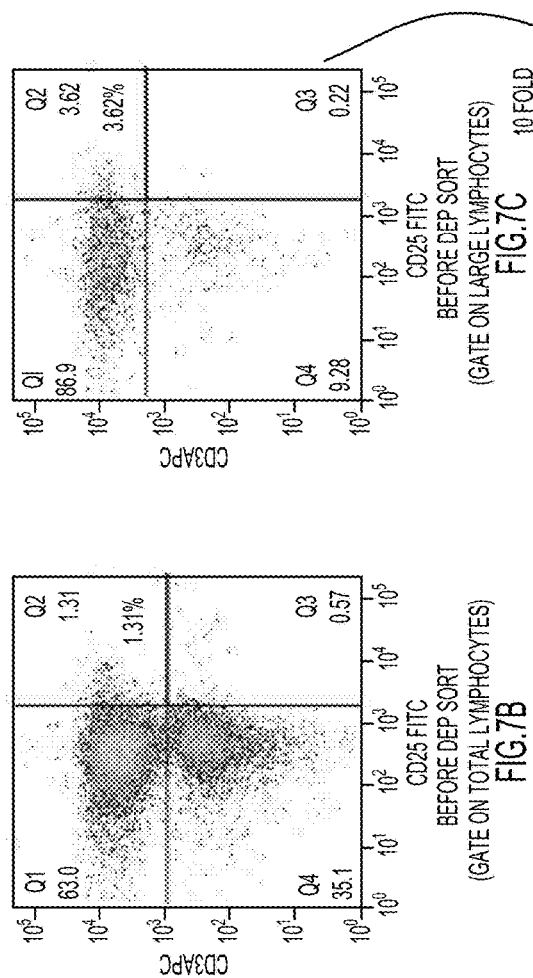
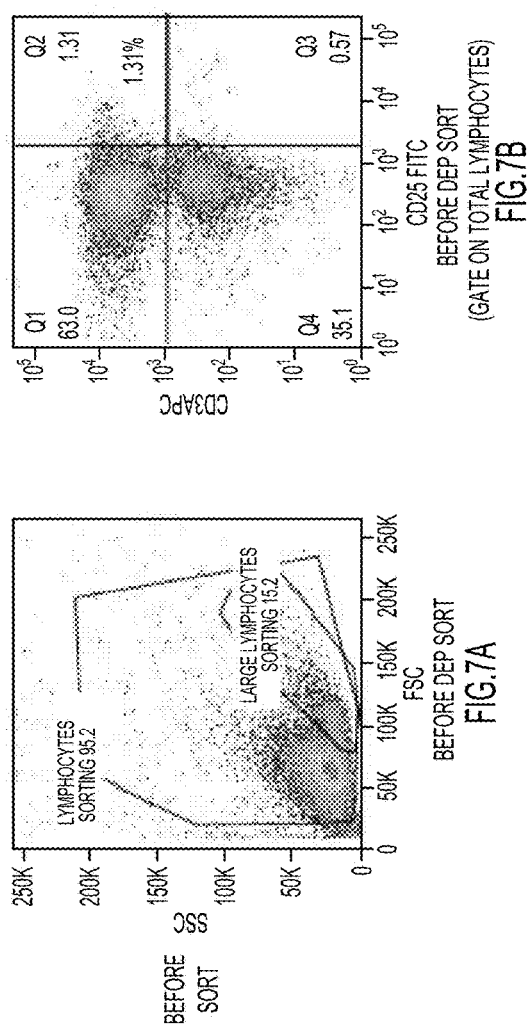
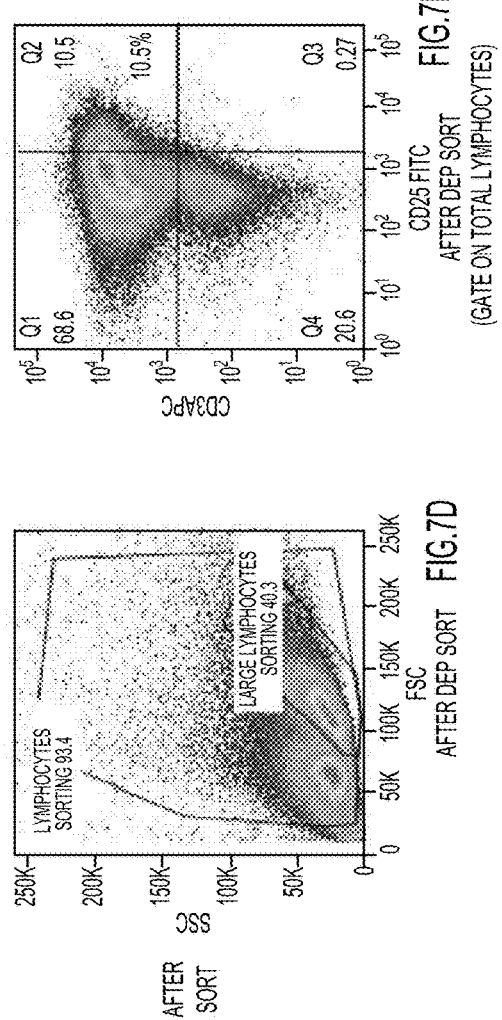

METHODS OF SORTING ACTIVATED T CELLS USING THREE DIMENSIONAL DIELECTROPHORESIS

CROSS-REFERENCE TO RELATED APPLICATIONS

This application claims priority to and benefit of U.S. Provisional Patent Application 62/424,348, filed on Nov. 18, 2016, which is incorporated herein by reference in its entirety for all purposes.

FIELD OF THE INVENTION

The field of the invention is cell sorting.

BACKGROUND

The background description includes information that may be useful in understanding the methods described herein. It is not an admission that any of the information provided herein is prior art or relevant to the presently claimed subject matter, or that any publication specifically or implicitly referenced is prior art.

The advent of molecular biology combined with various immunological techniques has led to the development of numerous therapeutic biologic agents, including monoclonal antibodies, fusion proteins, recombinant receptor antagonists, and more recently, CAR T-cell therapies. With the ongoing expansion of T cell based therapeutic approaches, techniques to isolate activated, functional T cells with high purity are needed in order to conduct various T cells assays, including activation, differentiation, expansion, and signaling assays.

Various cell sorting technologies exist for concentrating and isolating cells, including centrifugation, membrane filtration, fluorescence-activated cell sorting (FACS), magnetic-activated cell sorting (MACS), microfluidics, etc. Some of these techniques isolate or concentrate cells in bulk, e.g., such as centrifugation and filtration, while other techniques (e.g., FACS, MACS) allow higher selectivity.

Flow cytometry allows randomly distributed cells to be focused into a single continuous flow stream. Once in this continuous stream, each cell travels at an approximately identical speed, and passes through an optical detection zone for analysis based upon its optical properties (e.g., scatter and autofluorescence). Each cell passing through the optical detection zone may receive the same illumination intensity and time for reliable and consistent optical detection and analysis (see, e.g., Cram, Meth. Cell. Sci. (2002) 24(1): 1-9). In some cases, a modified type of flow cytometer, referred to as a fluorescence-activated cell sorter (FACS) may be employed. This type of device includes a sorting capability downstream of the optical detection zone, to select cells (e.g., expressing a fluorescent marker, labeled with a fluorescent tag, etc.) detected upstream.

Other approaches include using dielectrophoresis (DEP) for particle sorting. For example, a 3D, tunable, sheathless cell focusing and sorting DEP-based device has been used to separate particles based on size (see, Y. C. Kung et al., Small (2016) 12:4343; U.S. application Ser. No.: 15/484,964; U.S. Publication No.: 2015/0041325).

Despite the various techniques that are available for isolating cells, many of these techniques rely on modification of the cell, e.g., to express a fluorescent label, to be surface-labeled with a fluorescent marker, etc.), which is generally not desirable for therapeutic grade T cell production. Further, it is difficult to isolate activated T cells, e.g., from a non-activated T cells, in a manner that leads to high purity.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments are approximations, the numerical values set forth in the specific examples are reported as precisely as practicable. The numerical values presented in some embodiments described herein may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the subject matter described herein and claimed below and does not pose a limitation on the scope of the subject matter otherwise claimed. No language in the specification should be construed as indicating any non-claimed element essential to the practice of the claimed subject matter.

Groupings of alternative elements or embodiments of the subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY

The methods provided herein allow activated T cells to be isolated in a rapid manner with high purity, without modifying the T cells to express a fluorescent marker or undergo fluorescent tagging of a molecule on the surface of the T cell. Modifications to DEP-based cell sorting devices are also provided herein.

Methods are provided for sorting and collecting activated T cells using a device including a microfluidic channel comprising a plurality of electrodes configured to generate and apply dielectrophoretic (DEP) forces perpendicular to hydrodynamic flows along the microchannel in a manner that focuses and sorts cells based on size.

In an embodiment, CD4+ T cells are contacted with an anti-CD3 antibody and/or an anti-CD28 antibody under conditions suitable to cause activation of at least a portion of the population of CD4+ T cells. The CD4+T cells, which comprise both activated and non-activated T cells, are suspended in a fluid (e.g., a physiological buffer) and are flowed into a microfluidic channel.

In the first region of the microfluidic channel, the CD4+ T cells are focused into a single stream by applying dielectrophoretic (DEP) forces that are perpendicular to hydrodynamic flows along the microchannel. The first region of the channel comprises a first plurality of electrodes, disposed on surfaces of the microfluidic channel, configured to generate an electric field minimum at a first position within the microchannel. The cells are focused to the first position, where the electric field minimum occurs.

In a second region of the microfluidic channel, the CD4+ T cells are sorted based on size into activated CD4+ T cells and non-activated CD4+ T cells, also by applying dielectrophoretic (DEP) forces that are perpendicular to hydrodynamic flows along the microchannel. The second region of the channel comprises a second plurality of electrodes, disposed on surfaces of the microfluidic channel, configured to generate an electric field minimum at a second position within the microchannel, such that the larger, activated CD4+ T cells undergo lateral migration to reach the second position more quickly than the smaller non-activated CD4+ T cells.

The microfluidics channel splits into two channels, such that the larger (predominantly activated) CD4+ T cells that have undergone lateral migration exit a first channel, and the smaller (predominantly non-activated) CD4+ T cells exit a second microfluidics channel.

The methods, systems, and techniques provided herein may also be extended to CD8+ T cells.

In an embodiment, CD8+ T cells are contacted with an anti-CD3 antibody and/or an anti-CD28 antibody under conditions suitable to cause activation of at least a portion of the population of CD8+ T cells. The CD8+T cells, which comprise both activated and non-activated T cells, are suspended in a fluid (e.g., a physiological buffer) and are flowed into a microfluidic channel.

In the first region of the microfluidic channel, the CD8+ T cells are focused into a single stream by applying dielectrophoretic (DEP) forces that are perpendicular to hydrodynamic flows along the microchannel. The first region of the channel comprises a first plurality of electrodes, disposed on surfaces of the microfluidic channel, configured to generate an electric field minimum at a first position within the microchannel. The cells are focused to the first position, where the electric field minimum occurs.

In a second region of the microfluidic channel, the CD8+ T cells are sorted based on size into activated CD8+ T cells and non-activated CD8+ T cells, also by applying dielectrophoretic (DEP) forces that are perpendicular to hydrodynamic flows along the microchannel. The second region of the channel comprises a second plurality of electrodes, disposed on surfaces of the microfluidic channel, configured to generate an electric field minimum at a second position within the microchannel, such that the larger, activated CD8+ T cells undergo lateral migration to reach the second position more quickly than the smaller non-activated CD8+ T cells.

The microfluidics channel splits into two channels, such that the larger (predominantly activated) CD8+ T cells that have undergone lateral migration exit a first channel, and the smaller (predominantly non-activated) CD8+ T cells exit a second microfluidics channel.

In other embodiments, T cells (both CD4+ and CD8+) may be activated by antigens including but not limited to bacterial, viral and tumor antigens, in various forms.

BRIEF DESCRIPTION OF THE DRAWINGS

FIG. 4 shows an example protocol for generating activated CD4+ T cells from peripheral blood mononuclear cells.

FIGS. 5A-5B show microscopic images of non-activated versus activated CD4+ T cells.

FIGS. 7A-7F show data before and after various cell sorting assays using the 3D dielectrophoresis cell sorting device, illustrating enrichment of activated T cells, according to the embodiments provided herein.

DETAILED DESCRIPTION

Novel methods of isolating activated T cells are provided herein, using a 3D dielectrophoretic (DEP) cell sorting device. A mixture of activated CD4+ T cells and non-activated CD4+ T cells are introduced into the cell sorting device. In other embodiments, a mixture of activated CD8+ T cells and non-activated CD8+ T cells are introduced into the cell sorting device. The cell sorting device is configured to provide single-stream focusing of cells in an upper region of the device, and to sort based on size in a lower region of the device. The cell sorting device may also isolate cells in a high-speed flow. The cell sorting device comprises multiple exit channels, and the activated T cells are laterally deflected into an exit channel allowing collection with high purity. Various modifications of the 3D dielectrophoretic (DEP) cell sorting device are provided herein.

Dielectrophoresis (DEP) is a phenomenon in which a force is exerted on a particle in a non-uniform electric field. According to embodiments, if the cell is more polarizable than the medium, the cell may move towards a stronger electric field region, or if the cell is less polarizable than the medium, the cell may move towards a weaker electric field region. In some embodiments, larger cells experience a higher net force, and therefore, are deflected by DEP forces to a greater extent than smaller cells. Accordingly, cells of different sizes may be separated using DEP.

Figure 1:
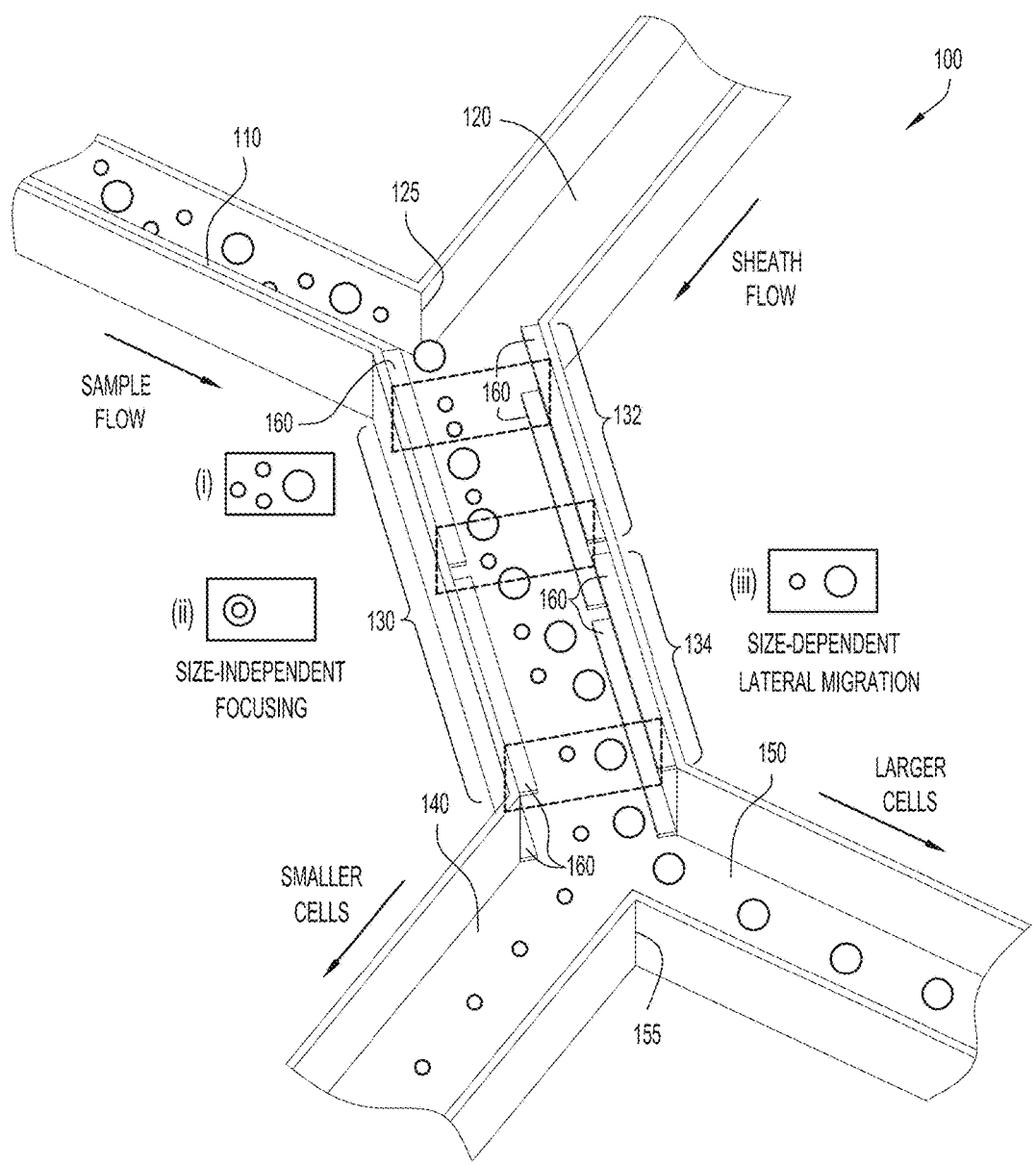
FIG. 1 is a schematic representation of an embodiment of a 3D dielectrophoresis cell sorting device comprising a microchannel. Cells of mixed sizes enter the microchannel. In the upper region of the microchannel, cells are focused into a single stream. In the lower region of the microchannel, cells are separated based on size. The larger cells, which experience stronger DEP forces, laterally migrate more than the smaller cells. At the exit of the microchannel, the larger cells are diverted into a collection channel for collection. To focus and sort cells, different AC signals are applied to corner electrodes positioned along the microchannel.

Referring to FIG. 1, an example implementation of a 3D dielectrophoretic (DEP) cell sorting device 100 is provided herein. Input channels 110 and 120 are fluidly coupled to a microfluidic channel 130, and microfluidic channel 130 is fluidly coupled to output channels 140 and 150. Component 125 represents a junction of the upper region of the microfluidic channel, wherein the two input channels converge. Component 135 represents the junction of the lower region of the microfluidic channel, wherein the two output channels diverge. Microchannel 130 comprises an upper region 132 (i) to (ii) and a lower region 134 (ii) to (iii). The upper region 132 focuses cells that enter the microchannel in a random spatial distribution into a single stream of cells, while the lower region 134 separates cells based on their respective size. Here, in the lower region 134, larger cells are laterally deflected to a greater degree than smaller cells, and the larger cells exiting the microchannel via output channel 150 are collected. Electrodes 160 are positioned at the upper and lower corners of the microchannel. In some aspects, region 132 comprises a first plurality of electrodes, and region 134 comprises a second plurality of electrodes, wherein the electrodes are not electrically connected. The plurality of electrodes, disposed on surfaces of the microfluidic channel 130 generate DEP forces suitable for focusing and separation of cells based on size. For a further description of 3D, continuously tunable, sheathless cell focusing DEP-based devices, the following reference is incorporated by reference in its entirety (see, Y. C. Kung et al., *Small* (2016) 12:4343). Provided herein are further modifications of a 3D DEP cell sorting device. Operational principles of DEP-based devices may also be found in Kung (Id.).

In some embodiments, the first plurality of electrodes (upstream) and/or the second plurality of electrodes (downstream) may receive signals of different amplitudes and/or different frequencies. For example, each signal applied to each of the electrodes of the first plurality of electrodes and/or of the second plurality of electrodes may be of a different amplitude and/or of a different frequency. In other examples, any two signals or any three signals applied to the electrodes of the first plurality of electrodes and/or of the second plurality of electrodes may be of a different amplitude and/or of a different frequency. In still other embodiments, signals applied to the corner electrodes may be A.C. signals of different amplitudes and of different frequencies.

The 3D dielectrophoretic (DEP) cell sorting device may be used to isolate activated T cells, or any other cell that undergoes a change in size (e.g., an increase in diameter of greater than or equal to 1 μm). Additional features of the cell sorting device are described as follows.

Input channel 110 provides a sample flow comprising a mixture of cells of various sizes suspended in a fluid, which may be a physiological buffer. The fluid acts to provide sample flow along the microchannel 130. In some embodiments, input channel 110 and input channel 120 converge at junction 125, at the input of microchannel 130. Input channel 120 may comprise a sheath flow, which is a bulk flow utilized to assist with cell focusing. In some aspects, the sheath flow of input channel 120 travels at a higher velocity than the sample flow of input channel 110. In other aspects, the width of the input channel 110 is less than the width of the input channel 120. One or both of these factors (the speed of the sheath flow and the volume of sheath flow), may act to focus the cells into a hydrodynamically focused stream. Thus, in some embodiments, focusing is accomplished with assistance from sheath flow, while in other embodiments, focusing is obtained without assistance from sheath flow.

Upon exiting input channel 110 and/or input channel 120, the cells enter microchannel 130, which comprises an upper region and a lower region, each region with electrodes arranged at upper corners and at lower corners. The first region comprises a first plurality of electrodes disposed to provide dielectrophoretic (DEP) forces perpendicular to hydrodynamic flows through the first region of the microfluidic channel. The second region, which is positioned downstream from the first region, also comprises a second plurality of electrodes disposed to provide dielectrophoretic (DEP) forces that are also perpendicular to hydrodynamic flows through the second region of the microfluidic channel. In the first region, voltages are applied to the first plurality of electrodes to provide an electric field minimum at a first location or position with respect to the cross-section of the microfluidic channel, and in the second region, voltages are applied to the second plurality of electrodes to provide an electric field minimum at a second location or position with respect to the cross-section of the channel, wherein the first location and the second location are at different positions relative to the cross-section of the channel (see, e.g., FIG. 1). In some aspects, the first plurality of electrodes and the second plurality of electrodes are not electrically coupled to one another, such that a first set of voltages can be supplied to the first set of electrodes and a second set of voltages can be supplied to the second set of electrodes.

In general, any location in the cross section of the microfluidic channel 130 can be selected as the focus position by varying voltages provided to the plurality of electrodes. Different combinations of voltages may be applied to the plurality of electrodes to focus the cell at a specific location (e.g., a position or location having a lateral, vertical, and diagonal component). Randomly distributed cells entering the microfluidic channel 130 are focused into a single stream, e.g., the position where the AC electric field minima is located. AC signals may be applied symmetrically or asymmetrically to the plurality of electrodes.

In some embodiments, microfluidic channel 130 comprises an upper and a lower substrate (e.g., glass substrates), with PDMS side walls. The middle of the microfluidic channel is an open channel through which fluid flows. Electrodes 160 may be configured to provide DEP forces perpendicular to hydrodynamic flows along the channel (see, e.g., FIG. 1). Cell focusing positions can be adjusted by changing voltage combinations applied to the electrodes, and may be adjusted in real time or near real time.

In some embodiments, the microfluidic channel 130 comprises a plurality of electrodes 160 disposed to provide dielectrophoretic (DEP) forces that are perpendicular to hydrodynamic flows along the channel. The cell sorting device 100 is configured to apply voltages to the plurality of electrodes 160 in order to generate an electric field minimum at a particular location, at which the cells are directed towards. In some embodiments, the electric field minimum is not centered in the microfluidic channel 130, and may be at any suitable position within the cross sectional area of the microfluidics channel 130.

The device may be configured to apply an AC voltage to one or more, to two or more, to three or more, or to all of the electrodes 160. In some embodiments, the device is configured to apply voltages independently to each of the electrodes 160.

In some embodiments, the device 100 comprises two pairs of electrodes disposed parallel to each other along the microfluidic channel 130. In other embodiments, the device 100 comprises electrodes disposed along the top and the bottom sides of the microfluidic channel 130. For example, the electrodes may be disposed along the midline of each side of the microfluidic channel 130, or along the midline of the top and the bottom of the microfluidic channel. In still other embodiments, the device 100 comprises two electrodes disposed along the corners of the top of the microfluidic channel and two electrodes disposed along the corners of the bottom of the microfluidic channel 130. In still other embodiments, the electrodes are arranged at a slanted angle at corners of the microfluidic channel.

Figure 3:
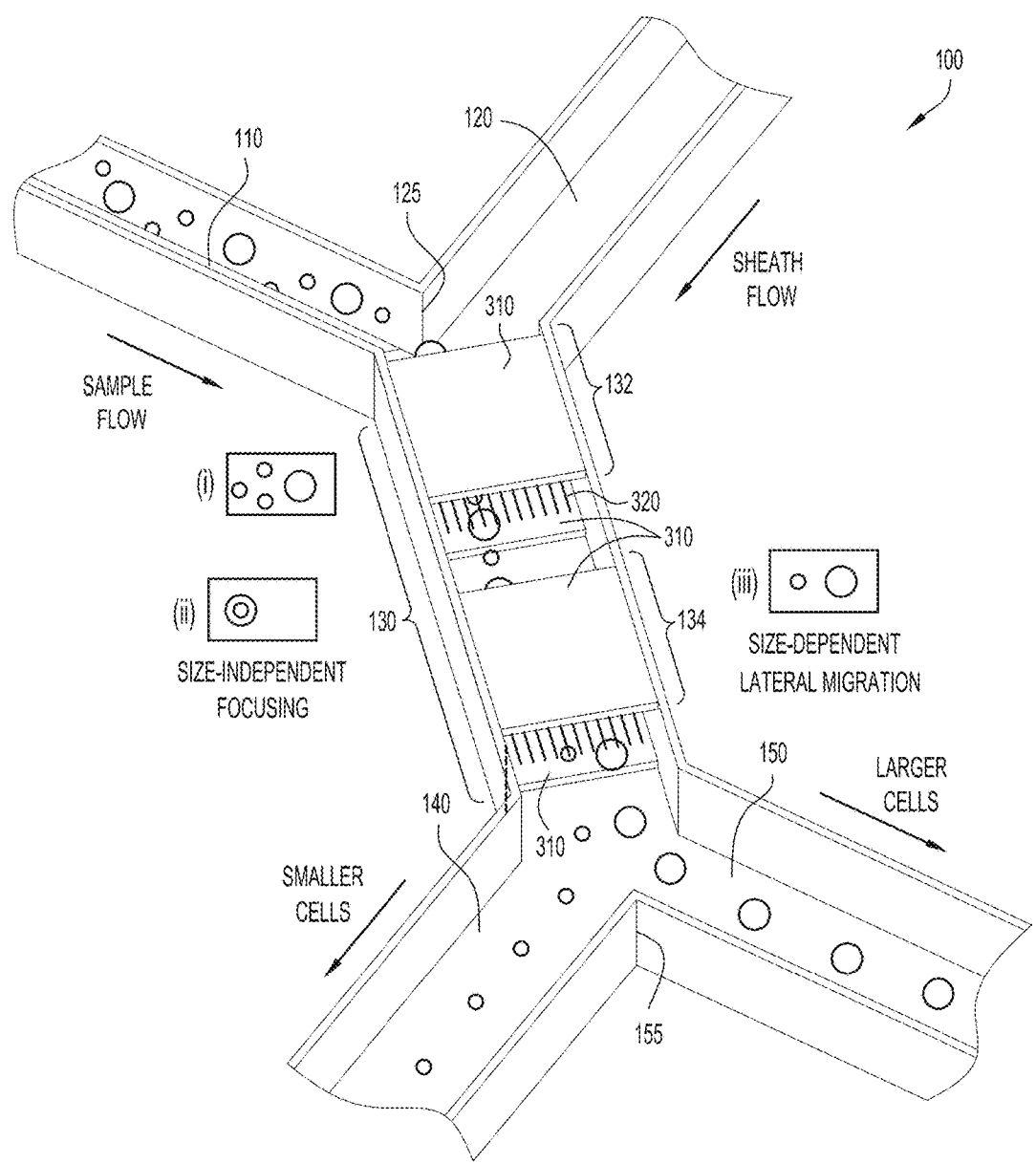
FIG. 3 is another example of an embodiment of a 3D dielectrophoresis cell sorting device comprising a microchannel, in which electrodes are replaced with a wire cage configuration, according to embodiments provided herein.

In still other embodiments, wire chambers along the length of the microfluidic channel may be utilized to generate DEP forces (in place of the electrodes) (see also, FIG. 3).

The device 100 may be configured to apply the AC voltages to the electrodes independently (e.g., using independently regulated voltage(s)) at a frequency ranging from about 0 Hz to about 500 MHz. In some embodiments, the frequency may range from any of the following: from about 1 Hz, from about 100 Hz, from about 1 kHz, from about 10 kHz, from about 50 kHz, from about 100 kHz, or from about 500 kHz up to any of the following: to about 1 MHz, to about 5 MHz, to about 10 MHz, to about 50 MHz, to about 100 MHz, to about 200 MHz, to about 300 MHz, to about 400 MHz, or up to about 500 MHz.

The device may be configured to apply the AC voltages to the electrodes independently (e.g., using independently regulated voltage(s)). In some embodiments, the voltage may range from about 0 V, from about 0.001 mV, from about 0.01 mV, from about 0.1 mV, from about 1 mV, from about 100 mV, from about 500 mV, from about 1 V, from about 5 V, from about 10 V up to about any of the following: 500 V, up to about 100 V, up to about 75 V, up to about 50 V, up to about 40 V, up to about 20 V, up to about 15 V. In some embodiments, any voltage may be applied, provided that the applied voltage is lower than a maximum voltage which would cause a fluid in the channel to undergo electrolysis, e.g., in some aspects, suitable voltages may range from about 1 V, from about 5V, from about 10V up to about any of the following: 100V, up to about 75V, up to about 50V, up to about 40V, up to about 20 V, or up to about 15 V.

The device 100 may be configured to provide voltages to the electrodes by any suitable technique, including integration of a voltage source (e.g., one or more power supplies, signal generators, etc.) into the device, integration of voltage regulators into the device configured to adjust one or more externally applied voltages, or any other technique for otherwise electrically coupling the device (and the electrodes in particular) to one or more external voltage sources (e.g., power supplies).

The electrodes may be configured (e.g., by applying voltages to the electrodes) to provide a field minimum anywhere within the channel, e.g., at or near a side, at or near a top, or at or near a bottom, at or near a diagonal line, at or near a midline, at or near the center, of the channel.

The microfluidic channel may have a length that can range from at least about 1 μm to at least about 10 cm. The microfluidic channel length may range from any of the following: at least about 1 μm, at least about 10 μm, at least about 100 μm, at least about 500 μm, at least about 1 mm, at least about 10 mm, at least about 1 cm, to any of the following: at least about 10 cm, at least about 25 cm, at least about 50 cm, at least about 75 cm, or at least about 100 cm.

The microfluidic channel or a portion thereof may assume any suitable shape, including linear, curved, serpentine, zigzag, etc. In some embodiments, the microfluidic channel 130 has a length greater than a linear length of the substrate in which the microfluidic channel is disposed. In other embodiments, the shape of the microchannel may be circular, oval, hexagonal, octagonal, etc.

The average depth of the microfluidic channel may range from about 0.1 μm to about 100 μm. Thus, the depth may range from any of the following: from about 0.5 μm, from about 1 μm, from about 10 μm, from about 20 μm, or from about 30 μm up to any of the following: to about 100 μm, to about 80 μm, to about 60 μm, to about 50 μm, or to about 40 μm.

The average width of the microfluidic channel may range from about 0.1 μm to about 500 μm or from about 0.1 μm to about 1 mm. Thus, the width may range from any of the following: from about 0.1 μm, from about 0.5 μm, from about 1 μm, from about 10 μm, from about 20 μm, from about 30 μm, from about 40 μm, from about 50 μm, from about 75 μm, or from about 100 μm to any of the following: up to about 1 mm, 500 μm, up to about 400 μm, up to about 300 μm, up to about 200 μm.

In general, the microfluidic channel 130 can be fabricated from any number of materials, e.g., including but not limited to, silicon, glass, plastic, elastomeric material, e.g., polydimethylsiloxane (PDMS), perfluoropolyethylene (a-PFPE), polyimides, polyolefin plastomers (POPs), polyurethane, and cross-linked NOVOLAC® (phenol formaldehyde polymer), etc., or any combination thereof.

It is understood that the channel dimensions provided herein are intended to be non-limiting and exemplary. For separations involving activated cells and non-activated cells, wherein the size difference between the activated cell and the non-activated cell is small (e.g., 1 μm diameter difference or less), the channel length may be extended to facilitate separation of the activated cells from the non-activated cells.

The lower region of the microfluidic channel may diverge into one or more output channels, e.g., output channels 140 and 150. Cells may exit microfluidic channel 130 and flow into two or more channels, whereby different sized cells flow into different channels based on the size and lateral deflection of the cell. For example, the microfluidic channel may diverge into 2, 3, 4, 5, 6, 7, 8, 9, 10, or more different channels. In the embodiment shown in FIG. 1, the microfluidic channel diverges into two output channels, with larger cells passing through output channel 150, and smaller cells flowing into output channel 140. Junction 155 may be positioned along the midline of the microchannel 130, or may be offset, such that the diameter of the output channel 150 is smaller than the diameter of the output channel 140. Thus, according to embodiments, non-activated T cells of a smaller size may exit output channel 140, and activated T cells of a larger size may exit output channel 150.

In some embodiments, the microfluidic channel 130 is fluidly coupled to a port or input channel 110 for introducing the cells into the upper region 132 of the channel. In other embodiments, the microfluidic channel is fluidly coupled to both a port or input channel 110 for introducing the cells and a port or channel 120 for introducing a sheath flow into the upper region of microfluidic channel 130. In some embodiments, the fluid coupling may be direct. In other embodiments, the fluid coupling may be indirect, e.g., through one or more valves, regulators, or other devices to prevent diffusion of the cells into the microfluidic channel.

In general, the device provides sub-micron precision with regard to focusing, e.g., cells may be focused to a position of less than about 0.2 µm. In some embodiments, cell size differences as small as 1 µm (or even smaller) can be separated with high purity (>90%), using the 3D DEP cell sorting device 100 provided herein.

In embodiments, the device may isolate activated T cells, such that the isolated T cells are of high purity (e.g., greater than about 90%, greater than about 95%, greater than about 96%, greater than about 97%, greater than about 98%, or greater than about 99%). In still other embodiments, the device may operate as a stand-alone device or may be incorporated with other components, e.g., as part of a lab on a chip.

Figure 2:
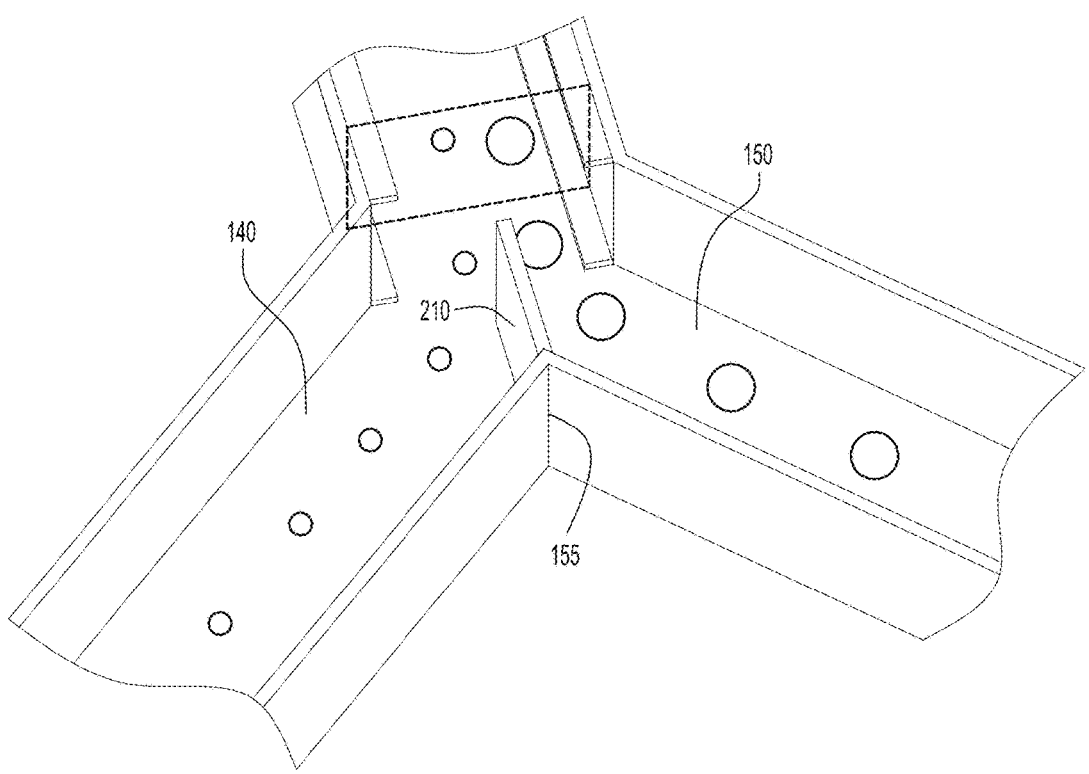
FIG. 2 is a schematic representation of another embodiment of a 3D dielectrophoresis cell sorting device comprising a microchannel, in which an adjustable separating component is positioned at the juncture of the two outlets to improve cell separation based on size.

FIG. 2 shows another embodiment of the cell sorting device 100. Microfluidic channel 130 divides into two output channels, output channel 140 and output channel 150. At juncture 155, an adjustable component 210 is provided to assist with separation of large cells from small cells. This component 210 may be any physical barrier (e.g., a divider, a diaphragm, a piezoelectric device, etc.) between the two diverging output paths. In this example, the adjustable component 210 is positioned between small cells flowing into output channel 140 and larger cells flowing into output channel 150. This adjustable component may be manually adjusted or may be adjusted by electrical or piezoelectric methods. In some aspects, the adjustable component can facilitate separation and increase purity when there is a small lateral separation distance between the activated and non-activated cells.

FIG. 3 is another embodiment of a 3D DEP cell sorting device according to the embodiments provided herein. In this example, a wire cage configuration has been provided to replace electrodes 160. The wire cage comprises an upper and lower cathode 310 with an array of wires 320 disposed between. Various AC voltages can be applied to the wires to generate areas of low potential, in order to create an electric field minimum.

For example, in this embodiment, the first plurality of electrodes in the upper region 132 of the microfluidic channel may be replaced with a first wire chamber comprising two cathode plates 310 and an array of wires 320 positioned in between, in a conductive medium, wherein each wire is coupled to an electrical source. The second plurality of electrodes in the lower region 134 of the microfluidic channel may be replaced with a second wire chamber comprising two cathode plates 310 and an array of wires 320 positioned in between, in a conductive medium, wherein each wire is coupled to an electrical source.

The device configurations provided herein are not intended to be limiting, but may encompass any configuration comprising electrodes, anodes, cathodes, wires, etc. which can be arranged to create a uniform electric field with a low potential area.

In other embodiments, the microfluidic channel may comprise a plurality of arrays of wires, e.g., such that each array of wires is arranged to lie within a plane, with the planes stacked at a repeating spacing interval within the microchannel. In other embodiments, the plurality of arrays of wires may be arranged such that each of the array of wires within a plane is rotated 90 degrees with respect to an adjacent array of wires within another plane.

Accordingly, methods of sorting activated T cells in a label free manner are provided, as sorting is based upon size and not the presence of a fluorescent signal. According to the methods provided herein, the upper portion of the microchannel provides high precision upstream focusing, and the lower portion provides high precision downstream size differentiation.

In some embodiments, a combination of DEP forces and fluid pulsing forces may be used to improve separation between activated and non-activated T cells. Fluid flow may be controlled by a fluid pump, e.g., to generate short or long pulses of fluid though the microfluidics channel. Smaller cells will move a greater distance under fluid pulsing conditions than larger cells. Polarity of the electrodes may be reversed to improve separation.

For example, DEP forces may be applied to activated and non-activated T cells using a first polarity with respect to the electrodes and associated with a continuous fluid flow. The DEP forces will cause the larger particles to migrate in a first direction, as larger particles experience higher DEP forces than smaller particles. After a period of time, the flow is stopped, and the polarity of the electrodes is reversed. A short series of fluid pulses are applied, and the smaller cells are displaced more than the larger cells in a second direction (generally opposite to the first direction). The polarity is reversed to its original configuration, and the process is repeated, with DEP forces and continuous flow applied for a period of time, driving the larger particles in the first direction. Again, fluid flow is stopped and the polarity is reversed. A series of fluid pulses are generated driving the smaller cells in a second direction (e.g., the opposite direction). This process may be repeated multiple times, to widen the gap between the small cells and the larger cells in the microfluidics channel.

EXAMPLES

The following examples are illustrative but not limiting of the methods and devices described herein.

Example 1

DEP Cell Sorting

FIG. 1 shows a device 100 configuration in which cells exposed to DEP forces in an upper region 132 of the microfluidics channel 130 for a sufficient amount of time migrate to form a focused stream (at a location of an electric field minimum), e.g., under high-speed flow conditions.

For each region 132, 134 of the microfluidic channel, two sets of two pairs of electrodes are disposed parallel to each other, such that these four electrodes (quadro-electrodes) are positioned at the top and the bottom corners of the channel. Four independently tunable AC signals are applied to the quadro-electrodes to create a tunnel-shape potential energy landscape with a cross-sectional single minimum along the channel.

Due to the perpendicular and decoupled nature of DEP forces and hydrodynamic forces, cells migrate in a transverse direction, driven by DEP forces, to a focusing location independently of the flow speeds in the microfluidic channel. As long as the microfluidic channel is of sufficient length to permit migration of the cells to the field minimum, the cells will migrate to the same location regardless of flow speed and/or cell size. In some embodiments, the focused location is also cell type independent as long as the cells show negative DEP responses to the applied electrical signals. Further, mammalian cell focusing can be achieved in physiological buffers (e.g., in a Ringer's solution, etc.). The cells do not need to be in low ionic buffers prior to DEP sorting, which is advantageous, as suspending cells in low isotonic buffers for long periods of time may decrease viability of cells.

The magnitude of the DEP force is linearly proportional to the gradient of electric field strength and the volume of cells. Cells that are more polarizable than the respective medium in which the cells are flowing, may experience positive DEP forces that move the cell towards the strong or stronger electric field region. Conversely, cells that are less polarizable than the respective medium in which the cells are flowing, may experience negative DEP forces that direct the cell to a weak or weaker electric field region. Providing an extended channel length allows cells in physiological buffers with weak negative DEP forces to have sufficient time to migrate to the focused location in high-speed flows.

To achieve continuous and high precision sorting, the device utilizes a first region in which all cells of different sizes are three-dimensionally focused (at a first focusing position) into a single-stream in a continuous flow, so that the differently sized cells have exactly or almost exactly the same reference position. The device also utilizes a second region, in which cells of different sizes laterally migrate (to a second focusing position), as cells of different sizes experience DEP forces of different magnitudes. Once reaching the second focusing position, cells may be sorted and collected based on size. Thus, size-independent, upstream cell focusing with a small deviation is needed for downstream high purity sorting of cells with small differences in size.

In some embodiments, sorting is achieved at flow speeds ranging from 1 cm/s to 10 cm/s in regular physiological buffers.

Example 2

Activation of Naïve CD4+ T Cells

FIG. 4 shows an experimental process flow for obtaining activated CD4+ T cells. Peripheral blood mononuclear cells (PBMC) were obtained. In some cases, the sample was frozen and underwent thawing before further processing. Once the PBMCs were at a suitable temperature, the cells underwent magnetic sorting to isolate CD4+ T cells from other cells present in the blood sample. The population of CD4+ T cells isolated by magnetic sorting included cells of various sizes, many of which were not activated.

After magnetic sorting, the CD4+ T cells are subjected to stimulation with an anti-CD3 and an anti-CD28 antibody. Protocols for activating/stimulating CD4+ T cells are known in the art. All such techniques are contemplated for use herein. For example, Guo (Nat Commun. (2016) 7:10307) showed that naïve CD4+ T cells were activated by anti-CD3 antibodies and anti-CD28 antibodies. Naïve CD4+ T cells, stimulated with anti-CD3 antibodies and anti-CD28 antibodies, upon TCR ligation, were shown to increase in size, e.g., up to double their diameter within about 24 hours.

An example protocol for stimulating T cells may be found in Guo (Id.). In this protocol, T cells were activated with anti-CD3 (2c11) antibodies and anti-CD28 (27.51) antibodies under culturing conditions, e.g., in Bruff's medium supplemented with 10% (vol/vol) FBS and 1% (vol/vol) penicillin/streptomycin for 24 hours or longer. In some aspects, the T cells were shown to increase in size over a period of 1 to 4 days, and on average, showed a doubling of their diameter.

FIGS. 5A-5B show microscopic images of activated (FIG. 5B) and non-activated (FIG. 5A) CD4+ T-cells. The non-activated panel shows that non-activated T cells are on average much smaller than activated T-cells shown in the right panel.

Once the cells were appropriately activated, the cells were loaded into the DEP based cell sorting device for separation of the activated T cells from the non-activated T cells.

The protocols provided herein or a modification thereof may also be used for activation of CD8+ T-cells.

Example 3

Sorting of T Cells

In this example, a low conductivity medium was used, 0.1× PBS (about 0.1 S/m). The average velocity of cells traveling through the microfluidic channel was 8 cm/s, and applied AC voltages had a frequency of 5 MHz and 25Vpp. The Qsheath:Qsample ratio was 2:1. In general, the conductance of the medium may range from about $10^{-6}$ S/m to about 5 S/m, from about 0.1 S/m to about 1 S/m, or any value in between.

Figure 6:
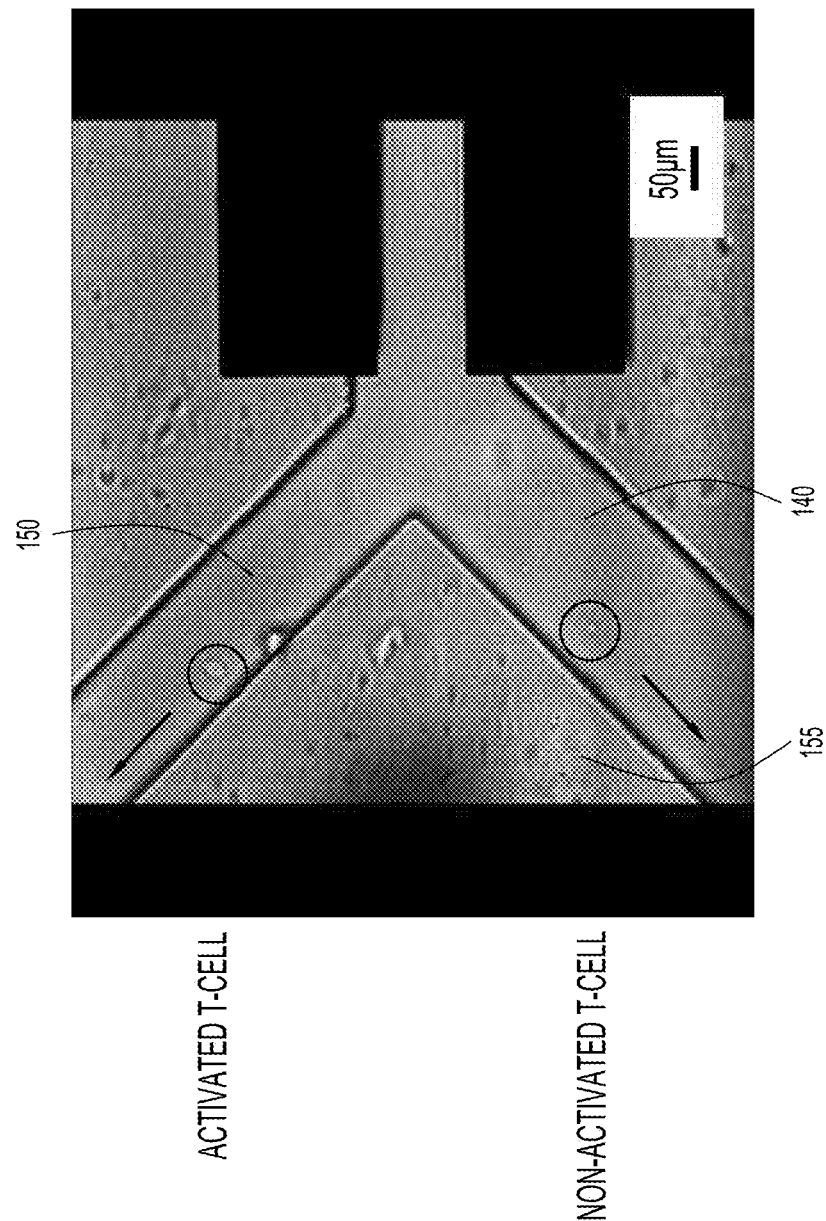
FIG. 6 shows a microscopic image of separation of activated CD4+ T cells from non-activated CD4+ T cells, using a 3D dielectrophoresis cell sorting device comprising a microchannel, according to the embodiments provided herein.

FIG. 6 shows an example DEP size sorting device that separated activated T-cells from non-activated T-cells. In this figure, the larger activated T cells were deflected laterally to a greater extent than the smaller non-activated T cells. Thus, the activated T cells were shown to exit a different channel (channel 150) than the non-activated T cells. In this example, the overall cross-sectional area of the output channel 150 which collected activated T cells was smaller than the overall cross-sectional area of the output channel 140 which collected non-activated T cells.

FIGS. 7A-7F show various panels of activated T-cells and non-activated T-cells. FIGS. 7A, 7B, and 7C show populations of activated T cells before DEP sorting. FIGS. 7D, 7E, and 7F show populations of activated T cells after DEP sorting. Cells may undergo multiple rounds of sorting using the DEP based device, until a suitable purity has been reached, e.g., by sending the cells collected from output channel 150 into input channel 110. In some embodiments, a 10 fold enrichment was achieved from a single round of DEP-based cell sorting.

The protocols provided herein or a modification thereof may also be used for sorting of CD8+ T-cells.

Example 4

Device Fabrication

FIGS. 8A-8H show a schematic of an example process flow for manufacturing the DEP size sorting device (see also, Kung et al. *Lab Chip* (2014) 15: 1861-1868). Any suitable technique known in the art may be utilized for fabrication of the device. In general, a PDMS thin film having an open microchannel is positioned between an upper and lower glass slide, each having electrodes positioned along the four corners of the channel. This configuration provides for the generation of a 3D electric field, which generates forces perpendicular to the microfluidic channel.

Figure 8A:
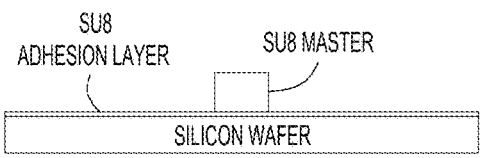
FIGS. 8A-8H show a schematic illustration of an example fabrication process to form the microchannel of the 3D dielectrophoresis cell sorting device, according to the embodiments provided herein.

FIG. 8A shows fabrication of SU-8 master mold on a silicon wafer using photolithography. The master mold is surface treated with trichloro (1H,1H,2H,2H-perfluorooctyl) silane (97%, Sigma-Aldrich, USA), also called PFOCTS, to facilitate demolding in a subsequent step (see, FIG. 2C).

Figure 8D:
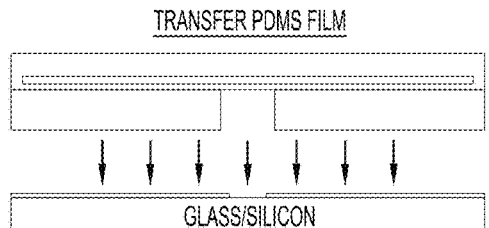
Figure 8B:
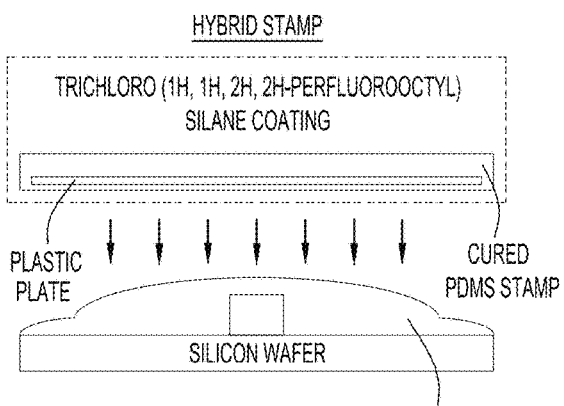

In FIG. 8B, an uncured PDMS mixture is poured onto the master, and a hybrid stamp is pressed against the uncured PDMS mixture.

A silicone elastomer mixture (PDMS/Sylgard 184, Dow Corning Corporation, Miland, USA) is prepared, using a weight ratio of base:curing agent of 10:1. A thin layer of the polydimethylsiloxane (PDMS) mixture, having a thickness of roughly 30 μm is placed between a petri dish and a polystyrene plastic plate (e.g., under 3 psi). The plastic plate together with the thin PDMS layer on its surface (the hybrid stamp) is peeled from the petri dish (FIG. 8B), and is surface treated with PFOCTS for 6 hours.

Additional uncured PDMS is poured into the petri dish, to cover the SU8 master, and is cured at 60° C. for 12 hours.

Figure 8E:
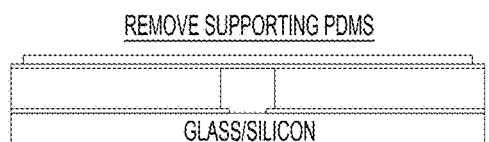
Figure 8F:
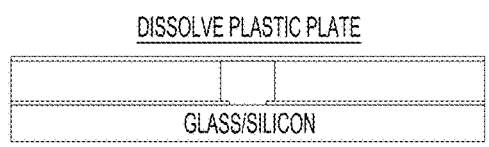
Figure 8C:
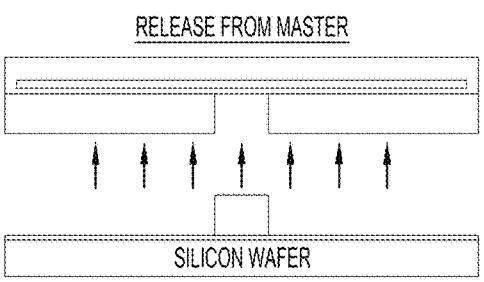

FIG. 8C shows demolding of the PDMS film from the master mold. The cured PDMS thin film adheres more strongly to the hybrid stamp than to the master mold, due to less PFOCTS treatment of the hybrid stamp than the master mold, allowing PDMS film to be separated from the master.

FIG. 8D shows transfer of the PDMS thin film to the glass/silicon bottom slide. Both the PDMS thin film of the hybrid stamp and the glass substrate comprising strip electrodes are treated with oxygen plasma to promote bonding. The channel is aligned with strip electrodes.

Figure 8G:

FIGS. 8E-8G show removal of the hybrid stamp by peeling off the bulk PDMS from the plastic plate (FIG. 8E), followed by dissolving the polystyrene plastic plate in an acetone bath for 4 hours (FIG. 8F). The thin residual PDMS film left on the substrate can be easily peeled from the device due to prior PFOCTS treatment (FIG. 8G) to complete the transfer.

Figure 8H:
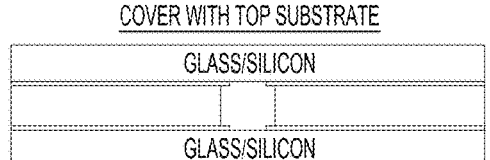

FIG. 8H shows alignment and placement of a top glass/silicon coverslip comprising strip electrodes. Oxygen plasma bonding may be used to complete device fabrication.

The techniques provided here are suitable for transferring PDMS thin films with fragile substrates, such as a high aspect ratio vertical wall, while maintaining mechanical integrity of the substrate.

It should be apparent to those skilled in the art that many more modifications besides those already described are possible without departing from the concepts described herein. That subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

It is understood that the examples and embodiments described herein are for illustrative purposes only and that various modifications or changes in view of the disclosure provided herein will be suggested to persons skilled in the art and are to be included within the spirit and purview of this application and scope of the appended claims.

What is claimed is:

1. A method of collecting activated CD4+ T cells and/or activated CD8+ T cells using a cell sorting device comprising a microfluidic channel comprising:
    contacting CD4+ T cells and/or CD8+ T cells with an antigen under conditions suitable to cause activation of at least a portion of the CD4+ T cells and/or CD8+ T cells;
    flowing the contacted CD4+T cells and/or CD8+ T cells, suspended in a fluid, into the microfluidic channel;
    focusing, in the upper region of the microfluidic channel, the CD4+ T cells and/or CD8+ T cells into a single stream by applying dielectrophoretic (DEP) forces that are perpendicular to hydrodynamic flows along the upper region of the microfluidic channel, wherein the upper region comprises a first plurality of electrodes, disposed on surfaces of the microfluidic channel, and configured to generate an electric field minimum at a first location;
    sorting, in a lower region of the microfluidic channel, the CD4+ T cells and/or CD8+ T cells into activated CD4+ T cells and/or activated CD8+ T cells and non-activated CD4+ T cells and/or non-activated CD8+ T cells by applying dielectrophoretic (DEP) forces that are perpendicular to hydrodynamic flows along the lower region of the microfluidic channel, wherein the lower region comprises a second plurality of electrodes, disposed on surfaces of the microfluidics channel, and configured to generate an electric field minimum at a second location such that the activated CD4+ T cells and/or activated CD8+ T cells undergo lateral migration to reach the second location; and
    collecting the activated CD4+ T cells and/or activated CD8+ T cells that laterally migrate to the second location.

2. The method of claim 1, wherein the antigen is selected from the group consisting of: an anti-CD3 antibody and/or an anti-CD28 antibody, a bacterial antigen, a viral antigen, and a tumor antigen.

3. The method of claim 1, wherein the antigen is an anti-CD3 antibody and an anti-CD28 antibody.

4. The method of claim 3, wherein contacting comprises contacting CD4+ T cells and/or CD8+ T cells with an anti-CD3 antibody and an anti-CD28 antibody for a period of time of up to four days.

5. The method of claim 1, wherein the CD4+ T cells and/or CD8+ T cells undergo a size change which increases their respective sizes between about 25% to about 200%.

6. The method of claim 1, wherein the hydrodynamic flows are at a rate ranging from about 10 μm/s to about 10 m/s.

7. The method of claim 6, wherein the hydrodynamic flows are at a rate ranging from about 1 cm/s to about 20 cm/s.

8. The method of claim 1, wherein the fluid comprises a medium having a conductance that ranges from about $10^{-6}$ S/m to about 5 S/m.

9. The method of claim 8, wherein the fluid comprises a medium having a conductance that ranges from about 0.1 S/m to about 1 S/m.

10. The method of claim 1, wherein the fluid comprises a physiological buffer.

11. The method of claim 1, wherein focusing comprises:
configuring the first plurality of electrodes by applying a first set of signals to the plurality of electrodes to produce an electric field minimum positioned in one half of the microfluidic channel; and
configuring the second plurality of electrodes by applying a second set of signals to the plurality of electrodes to produce an electric field minimum positioned in the other half of the microfluidic channel.

12. The method of claim 1, wherein the cell sorting device is configured to apply signals independently to each electrode of the plurality of electrodes.

13. The method of claim 1, wherein the cell sorting device comprises two pairs of electrodes disposed parallel to each other on a surface of the microfluidic channel.

14. The method of claim 13, wherein the first pair of electrodes are disposed at or near the top of the microchannel and the second pair of electrodes are disposed at or near the bottom of the microchannel.

15. The method of claim 1, further comprising applying an AC voltage to each electrode of the plurality of electrodes.

16. The method of claim 1, wherein the microfluidic channel has a shape selected from the group consisting of: a linear channel, a serpentine channel, a curved channel, and a zig-zag channel.

17. The method of claim 1, wherein the length of the first region of the microfluidics channel is sufficient to permit the activated CD4+ T cells and/or the activated CD8+ T cells to focus in the channel at a first location that is off center, wherein the first location is the first location of the electric field minimum.

18. The method of claim 1, wherein the length of the second region of the microfluidics channel is sufficient to permit the activated CD4+ T cells and/or the activated CD8+ T cells to focus in the channel at a second location that is off center, wherein the second location is the second location of the electric field minimum.

19. The method of claim 1, wherein the second region of the microfluidics channel diverges into a plurality of output channels, whereby different sized cells are diverted into different output channels.

20. The method of claim 1, wherein the second region of the microchannel diverges into two different output channels.

21. The method of claim 1, wherein the device comprises a first port or first channel for introducing the CD4+ T cells and/or the CD8+ T cells into the first region of the microfluidic channel.

22. The method of claim 1, wherein the device comprises a second port or second channel for introducing a sheath flow into the first region of the microfluidic channel.

23. The method of claim 11, wherein the signal comprises a voltage.

24. The method of claim 11, wherein the signal comprises a frequency and an amplitude.

25. The method of claim 11, wherein for the first plurality of electrodes and for the second plurality of electrodes, the signals applied to corner electrodes may be of a different amplitude and/or of a different frequency.

* * * * *